Patented Apr. 13, 1943

Plant Pat. 575

UNITED STATES PATENT OFFICE

575

NECTARINE

Frederic W. Anderson, Merced, Calif.

No Drawing. Application October 20, 1941, Serial No. 415,749

1 Claim. (Cl. 47—62)

The present invention relates to a new and distinct variety of nectarine of unusual eating quality in both the fresh and dried state.

This nectarine is one of many arising from crosses between the J. H. Hale peach and Lippiat nectarine, the object being to obtain larger and better shipping varieties. Older yellow fleshed varieties such as Boston, Humboldt, Lippiat, Pitmaston Orange and Hunter were too soft in flesh and too small to ever attain any commercial importance in California. This variety was one of a large number of nectarine seedlings of the second generation of this cross and has been firm and large enough for profitable long distance commercial shipments.

As compared with Kim Nectarine (Plant Patent No. 173), this variety is quite similar and ripens at the same period but is an improvement in the following respects: It has leaves with reniform glands instead of glandless leaves and is more resistant to mildew and red spider; the fruit is smoother and of much better eating quality. Although not so firm as Kim it has arrived in good shape in eastern markets and has on every occasion thus far brought higher prices per package when both varieties were included in the same car.

As compared with Boston, this variety ripens about two weeks earlier, is much larger and more productive, has much more red color on the surface, is much less susceptible to shot hole fungus, mildew and delayed dormancy, and is firm enough to ship under refrigeration to all markets in this country. The Boston is so soft and small that it has never been a success commercially and has always been confined to home and local markets and even, for these, grown only to a very limited extent.

As compared with Lippiat, this variety is about two weeks earlier, is larger and a much heavier producer, probably because it has reniform glands giving off a secretion that causes excess moisture to shed rapidly and allowing less time for the spores of shot-hole fungus and mildew to germinate, while the Lippiat having eglandular leaves is extremely susceptible to these diseases. This variety is much less affected by delayed dormancy also.

As compared with Pitmaston Orange and Hunter, this variety ripens earlier in the season, is larger, much firmer in flesh and has much more external red color—all important characteristics for a shipping variety. The eating quality is also superior.

Although not so firm as Kim, it is much firmer than all common varieties of nectarines and bears about the same relation in regards to other varieties as does Elberta among peaches while Kim would be in about the same relative position as J. H. Hale.

The variety first fruited in 1934 and was immediately propagated asexually and is now producing commercial crops in the originator's orchard.

In view of the similarity of this nectarine variety to the Kim and the intangible nature of most of the novel characteristics, illustration of the nectarine is unnecessary, since the distinguishing characteristics are detailed in the following technical description wherein color terminology conforms with general dictionary standards.

Tree: Large and spreading resembling Elberta. Vigorous. Very productive and a regular bearer.

*Trunk.*—About average in smoothness and stockiness.

*Branches.*—Medium in size. Smooth but gradually become somewhat shaggy with age. Brown in shade but red where exposed to sunshine and gray with age.

*Lenticels.*—Medium in number and size.

*Leaves.*—Length varies from 6½ to 7 inches and 1⅝ to 1⅞ inches in width. Large. Acutely pointed. Thick. Smooth and rather light green, resembling J. H. Hale. *Margin*—crenate. *Petiole*—medium in both length and thickness. *Glands*—average number is four, reniform in shape, usually two on the petiole and two or three on the margin of the blade. No stipules.

*Flower buds.*—Large size, rather plump in appearance and lightly pubescent.

*Flowers.*—First and full bloom about the same as J. H. Hale in mid-season. Large, pink flowers much like Stanwick except that calyx cup interior is yellow in color.

Fruit: Ripens one week to ten days before J. H. Hale peach being hard ripe about July 25.

*Size.*—Medium to large in size and quite uniform, running largely to from 2⅛ to 2⅜ inches in all diameters when well grown.

*Form.*—Uniform and symmetrical in form. Globose to slightly oblate.

*Suture.*—A shallow line (like J. H. Hale).

*Ventral surface.*—Rounded strongly throughout both sides with equal lips.

*Cavity.*—Rounded and about ⅜ inch in depth and ¾ inch in breadth.

*Base.*—Rounded.

*Apex.*—Short and somewhat rounded with almost no point.

*Stem.*—Short but adheres strongly to stone like J. H. Hale peach.

*Skin.*—Medium in thickness and toughness. Tenacious to flesh with no tendency to cracking. The color is yellow in background but usually completely covered with red. No pubescence.

*Flesh.*—Yellow in color except for red at pit margin with yellow fibres. Only moderate amygdalin content and dries satisfactorily with little discoloration without use of sulphur. Texture medium to firm but melting with only a few rather fine fibres. Ripens evenly and uniformly, not becoming soft at apex prematurely as in many nectarine varieties. Flavor, slightly subacid, mild and vinous. Aroma is distinct. Eating quality very good to best.

Stone: Free.

*Fibres.*—Short and free.

*Size.*—Medium, averaging about 1⅓ inches in length, one inch in breadth, and ¾ inch in thickness.

*Form.*—Obovoid, cuneate toward base.

*Base.*—Straight. Hilum—oval. Apex—acute.

*Sides.*—Equal with surfaces regularly furrowed and ridged throughout.

*Ridges.*—Jagged with angular pits.

*Ventral edge.*—Thick with wing toward base.

*Dorsal edge.*—Full with deep groove. Ridges are interrupted on either side.

*Color of stone.*—Yellowish red becoming brown with age.

*Tendency to split.*—Very slight in any season yet encountered.

Use: Market, local, dessert, culinary, and drying.

*Keeping quality.*—Good.

*Resistance to insects.*—Good, particularly to thrips.

*Resistance to diseases.*—Medium. About as susceptible to curl and peach blight as Elberta, but more susceptible to brown rot at blooming time. Almost immune to mildew of both leaves and fruit.

*Shipping qualities.*—Medium to good about like Elberta but not so good as J. H. Hale peach or Kim nectarine. Both growers and packers are demanding it for planting and shipping.

I claim:

A new and distinct variety of nectarine substantially as described, having unusual eating and shipping qualities and which makes an attractive dried product without the use of sulphur.

FREDERIC W. ANDERSON.